(12) United States Patent
Surakanti et al.

(10) Patent No.: US 10,966,816 B1
(45) Date of Patent: Apr. 6, 2021

(54) CONNECTIVE TISSUE TO BONE INTERFACE SCAFFOLDS

(71) Applicant: Sparta Biopharma LLC, Madison, NJ (US)

(72) Inventors: Dushyanth R. Surakanti, Madison, NJ (US); Adam B. Yanke, Madison, NJ (US); Adam W. Martinez, Madison, NJ (US); Kurt W. S. Klitzke, Madison, NJ (US); Travis E. Entrop, Madison, NJ (US); Dimitrios J. Angelis, Madison, NJ (US); Eric A. Nauman, West Lafayette, IN (US); Darryl A. Dickerson, Miami, FL (US)

(73) Assignee: Sparta Biopharma LLC, Madison, NJ (US)

(*) Notice: Subject to any disclaimer, the term of this patent is extended or adjusted under 35 U.S.C. 154(b) by 0 days.

(21) Appl. No.: 17/015,043

(22) Filed: Sep. 8, 2020

Related U.S. Application Data

(60) Provisional application No. 62/923,470, filed on Oct. 18, 2019, provisional application No. 63/069,658, filed on Aug. 24, 2020.

(51) Int. Cl.
| | |
|---|---|
| *A61L 27/36* | (2006.01) |
| *A61F 2/08* | (2006.01) |
| *A61F 2/28* | (2006.01) |
| *A61F 2/30* | (2006.01) |

(52) U.S. Cl.
CPC .......... *A61F 2/0811* (2013.01); *A61F 2/2846* (2013.01); *A61L 27/3604* (2013.01); *A61L 27/3608* (2013.01); *A61F 2002/0823* (2013.01); *A61F 2002/0876* (2013.01); *A61F 2002/2835* (2013.01); *A61F 2002/30059* (2013.01); *A61F 2002/30448* (2013.01); *A61F 2210/0076* (2013.01); *A61F 2220/005* (2013.01); *A61F 2220/0075* (2013.01); *A61F 2250/006* (2013.01)

(58) Field of Classification Search
CPC .. A61F 2/28; A61F 2002/2839; A61F 2/2846; A61L 27/3608; A61L 27/365
See application file for complete search history.

(56) References Cited

U.S. PATENT DOCUMENTS

| | | |
|---|---|---|
| 5,899,939 A | 5/1999 | Boyce et al. |
| 6,030,635 A | 2/2000 | Gertzman et al. |
| 6,090,998 A | 7/2000 | Grooms et al. |
| 6,432,436 B1 | 8/2002 | Gertzman et al. |
| 6,652,593 B2 | 11/2003 | Boyer et al. |

(Continued)

FOREIGN PATENT DOCUMENTS

| | | |
|---|---|---|
| EP | 1424948 B1 | 12/2008 |
| WO | WO02/009597 A2 | 2/2002 |

(Continued)

OTHER PUBLICATIONS

Emerich et al.; Biocompatibility of poly (DL-lactide-co-glycolide) microspheres implanted into the brain, Cell transplanation, 8(1); pp. 47-58; Jan. 1999.

*Primary Examiner* — Suba Ganesan
(74) *Attorney, Agent, or Firm* — Shay Glenn LLP

(57) ABSTRACT

Connective tissue-to-bone interface scaffolds (e.g., ligament-to-bone interface scaffolds, tendon-to-bone interface scaffolds, etc.). These scaffolds may be a single integrated implant or may be a modular (e.g., two-part) implant system.

12 Claims, 8 Drawing Sheets

(56) References Cited

U.S. PATENT DOCUMENTS

| | | |
|---|---|---|
| 6,776,800 B2 | 8/2004 | Boyer et al. |
| 6,855,169 B2 | 2/2005 | Boyer et al. |
| 7,585,311 B2 | 9/2009 | Green et al. |
| 7,662,184 B2 | 2/2010 | Edwards et al. |
| 7,771,741 B2 | 8/2010 | Drapeau et al. |
| 7,931,692 B2 | 4/2011 | Sybert et al. |
| 8,012,174 B2 | 9/2011 | ElAttrache et al. |
| 8,148,329 B2 | 4/2012 | McKay et al. |
| 8,231,653 B2 | 7/2012 | Dreyfuss |
| 8,603,183 B2 | 12/2013 | Ding |
| 8,702,809 B2 * | 4/2014 | Nauman ............. A61L 27/3645 623/23.63 |
| 8,758,792 B2 | 6/2014 | Behnam et al. |
| 9,005,246 B2 | 4/2015 | Burkhart et al. |
| 9,066,994 B2 | 6/2015 | Scarborough |
| 9,220,596 B2 | 12/2015 | Cook et al. |
| 9,220,608 B2 | 12/2015 | McKay |
| 9,387,094 B2 * | 7/2016 | Manrique ............ A61B 17/866 |
| 9,415,136 B2 | 8/2016 | Behnam et al. |
| 9,480,567 B2 | 11/2016 | McKay |
| 9,486,500 B2 | 11/2016 | McKay |
| 9,486,556 B2 | 11/2016 | Shi |
| 9,717,587 B2 | 8/2017 | Dougherty et al. |
| 9,737,292 B2 | 8/2017 | Sullivan et al. |
| 9,788,950 B1 | 10/2017 | Weston et al. |
| 10,123,792 B2 | 11/2018 | Pilgeram |
| 10,172,651 B2 | 1/2019 | Emerton et al. |
| 10,172,703 B2 | 1/2019 | Adams et al. |
| 10,265,159 B2 | 4/2019 | Denham et al. |
| 2004/0030386 A1 | 2/2004 | Boyce |
| 2005/0015147 A1 | 1/2005 | Schwardt et al. |
| 2005/0136124 A1 | 6/2005 | Blum et al. |
| 2006/0079904 A1 | 4/2006 | Thal |
| 2007/0219558 A1 | 9/2007 | Deutsch |
| 2007/0288023 A1 | 12/2007 | Pellegrino et al. |
| 2008/0188936 A1 | 8/2008 | Ball et al. |
| 2009/0318960 A1 | 12/2009 | Burkhart |
| 2013/0079889 A1 | 3/2013 | Spillman |
| 2013/0122095 A1 | 5/2013 | Kestler et al. |
| 2016/0331368 A1 | 11/2016 | Ticker |
| 2017/0143551 A1 | 5/2017 | Coleman |
| 2017/0203006 A1 | 7/2017 | Carter et al. |
| 2018/0263755 A1 | 9/2018 | Adams et al. |
| 2018/0303616 A1 | 10/2018 | Bhattacharyya et al. |
| 2019/0151510 A1 | 5/2019 | Tasciotti et al. |

FOREIGN PATENT DOCUMENTS

| | | |
|---|---|---|
| WO | WO2006/060035 A2 | 6/2006 |
| WO | WO2006/096512 A2 | 9/2006 |
| WO | WO2008/157495 A2 | 12/2008 |
| WO | WO2012/027711 A2 | 3/2012 |
| WO | WO2017/075608 A1 | 5/2017 |
| WO | WO2019/043125 A1 | 3/2019 |

* cited by examiner

CONNECTIVE TISSUE TO BONE INTERFACE SCAFFOLDS

CROSS REFERENCE TO RELATED APPLICATIONS

This patent application claims priority to U.S. Provisional Patent Application No. 62/923,470, titled "CONNECTIVE TISSUE TO BONE INTERFACE SCAFFOLDS," filed on Oct. 18, 2019, and U.S. Provisional Patent Application No. 63/069,658, titled "CONNECTIVE TISSUE TO BONE INTERFACE SCAFFOLDS," filed on Aug. 24, 2020 each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are scaffolds for repair of the enthesis, including ligament to bone and tendon to bone interface scaffolds for repair of torn tendons, ligaments, and/or calcified and uncalcified fibrocartilage.

BACKGROUND

Connective tissues, including tendons and ligaments, provide joint stability, guide joint motion, and play an important role in proprioception. Injury to ligaments and tendons represents a major portion of all sports-related injuries on an annual basis. In particular, rotator cuff injuries are particularly prevalent and difficult to repair.

The rotator cuff is a group of muscles and tendons that surround the shoulder joint, keeping the head of your upper arm bone firmly within the shallow socket of the shoulder. A rotator cuff injury can cause a dull ache in the shoulder, which often worsens when you try to sleep on the involved side. Rotator cuff injuries occur most often in people who repeatedly perform overhead motions in their jobs or sports. Examples include painters, carpenters, and people who play baseball or tennis, although rotator cuff tears may occur as a result of a single injury. The risk of rotator cuff injury increases with age.

Extensive rotator cuff tears typically require surgical repair, however current techniques are not optimal, and may be difficult or impossible to achieve, or may fail days or months after surgery. In particular, reattachment of connective tissue, including rotator cuff tissue, to bone is notoriously difficult to achieve. In uninjured tissue, the interface between the soft connective tissue and the bone occurs through a complex and distinct interface having multiple layers. The first is the connective tissue proper, or midsubstance, which consists mostly of a type I collagen matrix. The midsubstance inserts into a layer of fibrocartilage mainly composed of type II collagen rich with proteoglycans. This layer transitions into calcified fibrocartilage layer. The final region is subchondral bone, which contained a mineralized type I collagen matrix. The junction between bone and soft connective tissue has controlled heterogeneity, permitting a gradual manner of load transmission from the hard tissue to the soft tissue in a manner hypothesized to minimize stress and strain concentrations. Studies using autografts have shown that using the soft connective tissue proper as the sole graft does not lead to strong biological integration and the re-establishment of the native bone-soft tissue interface. Without such integration, mechanical stability is limited at the joint and the lack of integration can produce higher rates of graft failure. In order to restore the physiological structure and function of the tissue, new strategies must be developed for the treatment of soft connective tissue ruptures.

Tissue engineering has emerged in the past twenty years as a promising strategy for soft connective tissue repairs. There have been a number of reports on the use of tissue engineering techniques to regenerate ligaments and tendons. However, most of these studies focus on the midsubstance region and fail to address the regeneration of the interface. To date, collagen fibers, silk fibers, collagen gels and synthetic polymer scaffolds have been utilized to replace the soft tissue portion of the ligament or tendon. One example is a composite collagen fiber-collagen gel scaffold seeded with fibroblasts that does not degrade in vitro and matches many of the mechanical properties of normal ligaments. Unfortunately for many tissues, especially those in the musculoskeletal system, matching the mechanical properties is not sufficient. In order to transmit loads, the construct must successfully integrate with the host tissue and revascularize, processes that are largely governed by the construct's permeability.

Current standard of care for reattaching connective tissues (ligament, tendon) to bone typically uses suture and suture anchors to reattach the connective tissue to the bone. Re-tearing of the connective tissue is common, and occurs in over half of the cases. Further, full mobility and pain relief are not generally possible.

Although bone implants for repairing damaged ligaments and tendons from bone have been proposed (e.g., U.S. Pat. Nos. 6,776,800, 6,855,169, 7,753,963, and 8,702,809), these implants have been difficult to implement. In particular, these implants have required hinge regions or other techniques for making them flexible, often compromising their strength and structural integrity and requiring complex fabrication processes. Thus, there is a need for a connective tissue-to-bone interface scaffolds that can easily be integrated into bone and revascularize, as well as provide attachment and ingrowth for the connective tissue. In particular, it is desirable to provide scaffolds that may be adapted for easy attachment and use.

SUMMARY OF THE DISCLOSURE

Described herein are connective tissue-to-bone interface scaffolds (e.g., ligament-to-bone interface scaffolds, tendon-to-bone interface scaffolds, etc.). These scaffolds may be referred to as grafts or implants, and may be a single integrated implant or may be a modular (e.g., two- or more part) implant system.

The connective tissue-to-bone interface grafts described herein are typically formed of a bone material that has been processed to form a layered structure having a first layer that is demineralized and porous and a second layer that is mineralized and porous. The graft may be a strip, having an elongate, flattened sheet or strip-like configuration, in which the first (e.g., upper) major side is mineralized and the second (e.g., lower) major side is demineralized. The edges between the first and second side (minor sides) may be rounded or beveled.

For example, in some variations the connective tissue-to-bone interface graft described herein may be formed of a bone allograft material that is derived from human bone (e.g., cancellous bone) and may have a length of between, e.g., 10-50 mm, a width of between 6-26 mm in width, and a thickness of between 1-6.5 mm. In some variations the physician may cut this shape (trimming the length and/or width) down to a different length and width for implantation. As mentioned, the second major side is demineralized to remove calcium and may be treated to prevent osteogenesis, allowing the connective tissue (e.g., in some variations of the rotator cuff) to heal directly to the implant on the demineralized side. The demineralized side may be formed mostly of type I collagen, similar to the tendon material. The opposite, first major side may remain mineralized, providing a hard, tissue-facing layer that enables osseointegration and fixation to the bone. The top side and the bottom side are typically continuous with each other and may be formed of the same original strip of material (e.g., formed of a unitary section of cancellous bone). Alternatively, in some variations the first layer (demineralized) and the second (mineralized) layers may be separately formed and attached, e.g., by an adhesive having the biocompatibility, strength and viscosity necessary to allow it to hold the mineralized portion to the demineralized portion without occluding the pores on either side.

As described herein, it may be particularly important to prevent occluding of the pores in either or both the mineralized and demineralized sides of the implant. The grafts described herein typically have a high porosity, allowing fluid conductance and rapid cell incorporation into the thickness of the graft. The porosity also promotes vascular ingrowth.

In use, the graft is affixed to the bone. For example, the bone site (the site of implantation) may be prepared first to receive the implant by exposing the bone and marrow in an attachment region (e.g., a cut-out region), then one or more anchors may be inserted into the humerus at the medial edge of the rotator cuff, then the scaffold may be attached to the anchors with the bone ingrowth side (the mineralized side) facing the bone. The graft may be secured in place further by suture knots (tying knots over the scaffold).

In general, it may be particularly beneficial to have the graft be configured to flexibility and compliance, so that it may be implanted, e.g., through a cannula, by folding or curling it, and also for allowing the graft to conform to the often irregular surface of the cut-our region of the bone. As described herein, the applicants have surprisingly found that this may be achieved by controlling the thickness of the mineralized region, e.g., so that it is much thinner than the demineralized region, and not greater than about 1.5 mm (e.g., is 1.5 mm or less, 1.4 mm or less, 1.3 mm or less, 1.2 mm or less, 1.1 mm or less, 1.0 mm or less, 0.9 mm or less, 0.8 mm or less, etc.). Thus, in general, the thickness of the mineralized layer may be different and often much less than the thicknesses of the demineralized layer forming the rest of the graft. For example, the thickness of the demineralized portion of the implant may be 55-99% (e.g., between about 60% and 99%, between about 60-95%, between about 55-95%, between about 55-80%, between about 55-75%, etc.) of the thickness of the graft (e.g., the implant or scaffold).

Although in some of the grafts described herein the body of the graft may be sufficiently 'soft' so that a needle may be passed through it, e.g., puncturing it, in any of the grafts described herein may be configured for insertion or implantation into the bone. For example, any of these implants may include one or more pre-formed suture holes or passages through or into the body of the implant. These suture openings or holes (or in some variations, channels) may be configured to allow suture to be threaded into and through the implant so that they be readily secured into the body, particularly into the bone tissue. In some variations the implant may be pre-threaded with one or more lengths of suture, which may greatly enhance the ease of use and may help guide the physician in attaching and positioning the implants. The pre-formed (e.g., drilled) holes may be treated to allow the suture to pass through but may prevent tearing or damage to the graft, particularly the softer, demineralized side.

Also described herein are multi-part grafts that may including multiple planar layers that are either preassembled (e.g., using an adhesive, suture, etc.) or may be used separately and attached. For example, the implants described herein may include a first layer that is mineralized that is attached (e.g., via an adhesive) either directly to a second layer of demineralized bone that may be complimentary to the first layer, or indirectly, e.g., through a third, intermediate layer. In some variations the first and second (or first, second and third) layers may be configured to engage with each other, e.g., via a formed attachment between the complimentary sides of the first and second (or first and third, second and third) layers. For example, the first layer may attachably couple to the second layer.

In general the grafts described herein may have a low stiffness (e.g., may be highly flexible), and a high compressibility and compliance. The flexibility and compliance may allow the graft to be inserted minimally invasively through a cannula or other introducer, despite having a mineralized outer surface that can interface with the bone. The high compliance of the graft may also allow it to conform to the bone (e.g., an attachment/cut-out region of the bone) more readily, which may improve outcomes.

For example, described herein are flexible, compressible and compliant grafts that may comprise a strip of bone forming a body having a length, a width and a thickness, wherein the thickness is less than half the length and half the width, the body further comprising: a first layer of demineralized bone extending the length and the width of the body; and a second layer of mineralized bone that is continuously adjacent to the first layer, wherein the second layer has a thickness that is less than 1.5 mm. In some variations the second layer is between about 1.2 mm and 0.1 mm thick. The second layer typically forms an outer surface of the graft. The second layer may have a substantially constant thickness, e.g., the thickness may vary by less than 10% (e.g., less than 9%, less than 8%, less than 7%, less than 6%, less than 5%, less than 4%, less than 3%, etc.) along the entire second layer. The thickness of the body may be, for example, between about 3.5 and about 6.5 mm. In any of these grafts, the density of the graft (e.g. the density of the body) may be less than 2.6e-4 $g/mm^3$.

For example, a flexible, compressible and compliant graft, may comprise a strip of bone forming a body having a length, a width and a thickness, wherein the thickness is between 4 mm and 6.5 mm and is less than half the length and half the width, the body further comprising: a first layer of porous demineralized bone extending the length and width of the body; and a second layer of porous mineralized bone extending along an outer surface of the strip that is continuously adjacent to the first layer, wherein the second layer has a constant thickness that is less than 1.5 mm; wherein the body has a density that is less than 2.6e-4 $g/mm^3$.

For example, a flexible, compressible and compliant graft may comprise a strip of bone forming a body having a length, a width and a thickness, wherein the thickness is between 4 mm and 6.5 mm and is less than half the length and half the width, the body further comprising: a first layer of porous demineralized bone extending the length and width of the body; and a second layer of porous mineralized bone extending along an outer surface of the strip that is continuously adjacent to the first layer, wherein the second layer has a thickness that is less than 1.5 mm that varies by less than 10% along the entire second layer; wherein the body had a density that is less than 2.6e-4 g/mm$^3$ and a mean bending thickness that is less than about 1.2 mNm.

The body of the graft may have a mean bending thickness that is less than about 1.2 mNm (e.g., less than about 1.1 mNm, less than about 1.0 mNm, less than about 0.9 mNm, less than about 0.8 mNm, less than about 0.7 mNm, less than about 0.6 mNm, less than about 0.5 mNm, less than about 0.1 mNm, etc.). Thus, the graft, particularly when hydrated prior to implantation, may be highly flexible, comparable to paper or newsprint, without breaking or disrupting the mineralized layer extending across the side.

As mentioned, any of these grafts may include one or more suture channels pre-formed through the thickness of the body.

The bone forming the graft may be any appropriate bone, including human (allograft) or non-human bone, such as porcine cancellous bone.

The edges of the body of the graft may be square or may be rounded, e.g., having a radius of curvature of between 0.25 mm and 2 mm. In some variations the edges of the body are beveled at an angle of between 30 and 60 degrees.

In any of the grafts described herein the first layer may have a different color than the second layer. This may allow immediate and easy recognition of the mineralized vs. demineralized sides of the graft, which may otherwise be difficult to distinguish. In some variations a biocompatible dye or coloring is used to mark or label one or both sides to indicate which is which.

As mentioned, the graft body may have a length of, e.g., between about 15 and 50 mm, and a width of, e.g., between about 10-25 mm. In general, the graft body may be substantially free of fat and blood proteins. In some variations the first layer (e.g., the demineralized layer) is substantially free of ostioinductivity.

In some variations, the mineralized (e.g., second) layer has 8% or more calcium, while the demineralized (first) layer has less than 8% calcium.

As mentioned, also described herein are methods of using any of these grafts to repair tissue, including (but not limited to) repair of a rotator cuff. For example, a method of repairing a rotator cuff may include: removing a region of a cortical layer of a humerus and/or forming microfractures in the humerous to expose a marrow material in an attachment region; anchoring one or more suture to the humerus; passing the one or more sutures through a thickness of a flexible, compressible and compliant graft, the graft having a length, a width and a thickness, wherein the thickness is less than half the length and half the width, the graft further comprising: a first layer of demineralized bone and a second layer of mineralized bone that is continuously adjacent to the first layer, wherein the second layer has a thickness that is less than 1.5 mm; securing the second layer of the graft in contact with the marrow material, wherein the second layer compliantly conforms to the attachment region (in some variations, so that fluid pressure from the humerous drives the marrow material to infiltrate the second layer); and suturing a tendon against the first layer. The thickness of the second layer may be between 1.2 mm and 0.1 mm. The graft may have a density that is less than 2.6e-4 g/mm$^3$.

The step of removing a region of the cortical layer and/or forming microfractures in the humerous may be done alternatively or additionally. For example, in some variations, the bone (e.g., humerous) is prepared by removing a region of the cortical layer, e.g., to form a shelf or landing pad region to which the graft may be attached. Alternatively, in some variations the bone (e.g., humerous) may be prepared by forming microfractures to the region to which the graft will be attached, without removing a region. In some variations both a region of the bone may be removed and the bone may be treated to form microfractures.

For example, a method of repairing a rotator cuff may include: removing a region of a cortical layer of a humerus and/or forming microfractures in the bone to expose a marrow material within an attachment region, wherein the region has a length of between 10 and 50 mm, a width of between 6 and 25 mm; anchoring one or more suture to the humerus; placing a flexible, compressible and compliant graft against the attachment region, the graft having a length, a width and a thickness, wherein the thickness is less than half the length and half the width, the graft further comprising: a first layer of demineralized bone and a second layer of mineralized bone that is continuously adjacent to the first layer, wherein the second layer has a thickness that is less than 1.5 mm; securing the graft to the humerus so that the second layer of the graft in contact with the marrow material and compliantly conforms to the attachment region, so that fluid pressure from the humerous drives the marrow material to infiltrate the second layer; and suturing a tendon against the second bone scaffold.

Suturing the tendon against the first layer may comprise suturing with the one or more sutures. Suturing the tendon may comprise suturing the tendons of one or more of: the supraspinatus muscle, infraspinatus muscle teres minor muscle or the subscapularis muscle.

Passing the one or more sutures through the thickness of the graft may comprise passing the one or more suture through holes pre-formed through the graft. Alternatively or additionally, the grafts described herein may permit a needle to be passed through the graft without requiring a pre-formed hole.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 7E shows the graft between two fingers in an uncompressed configuration. FIG. 7F shows the same graft being compressed between two fingers.

DETAILED DESCRIPTION

Described herein are connective tissue-to-bone interface scaffolds (e.g., grafts) that are adapted and configured for surgical implantation onto bone to allow ingrowth of both bone as well as connective tissue. These grafts may be particularly well adapted for implantation and attachment as part of a minimally-invasive, e.g., arthroscopic, laparoscopic, surgery.

Figure 1:
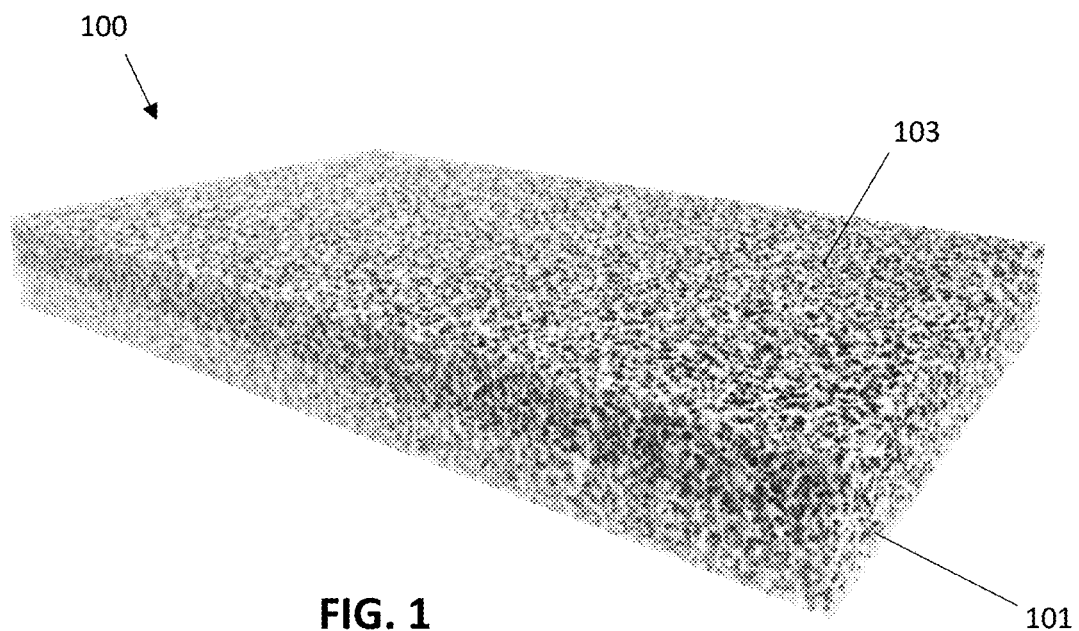
FIG. 1 is an example of a bone scaffold having a layer of demineralized and a layer of mineralized bone as described herein.

For example, FIG. 1 shows one example of a tissue-to-bone interface scaffold as described herein 100. In FIG. 1, the scaffold includes a first, demineralized layer 101 and a second mineralized layer 103. As will be described in detail below, the dimensions of the mineralized and demineralized layers, and in particular, their ratios, may be selected within a desired range to optimize both the ease of using them in the particular surgical procedures described herein, as well as for stability and in-growth of connective tissue and/or bone. In FIG. 1 the mineralized and demineralized portions are both porous, although they may have different porosities. For example, the porosity of the mineralized side of the implant may be greater than (or the same as) the porosity of the demineralized side, and may be configured or selected to permit the fluid pressure from the humerus to drive bone marrow into the scaffold (e.g., into the cancellous side of the scaffold). In some variations the implant may be configured to limit the migration of the bone marrow into the demineralized side, e.g., by limiting the porosity and/or by treatments to limit migration (including treatments to reduce the side, modify the surface properties, provide a barrier to migration, etc.). In some variations the scaffold may be configured to permit migration of the bone marrow into the demineralized side.

In general the bone scaffold may be at least two layers, e.g., the demineralized layer and the mineralized layer, that are immediately adjacent to each other. The scaffold may be shaped and sized so that it may be inserted or implanted into the body, as will be described in greater detail below, as well as providing optimal attachment to the bone and connective tissue.

Figure 2A:
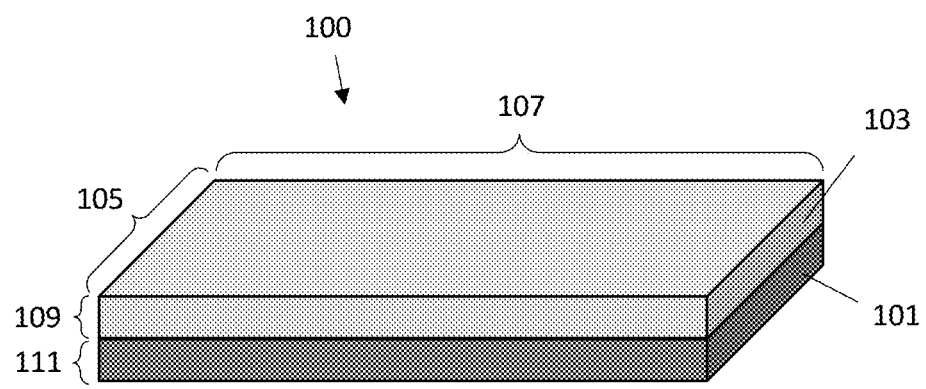
FIGS. 2A-2E illustrate example of biocompatible bone scaffolds as described herein.
Figure 2B:
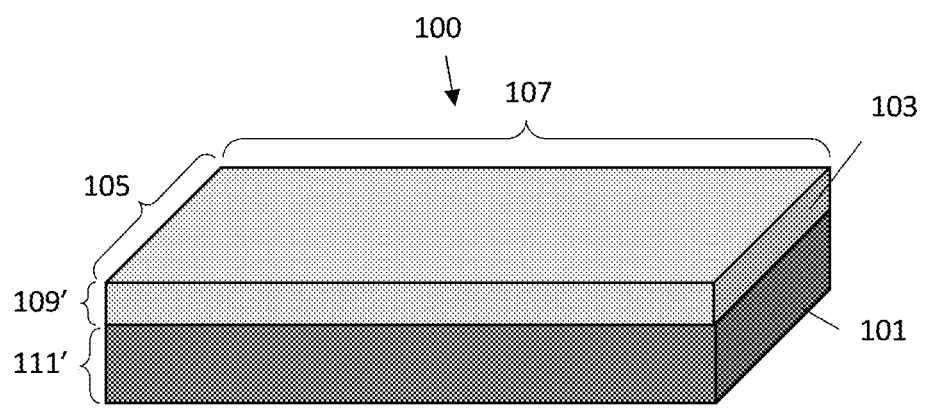
Figure 2C:
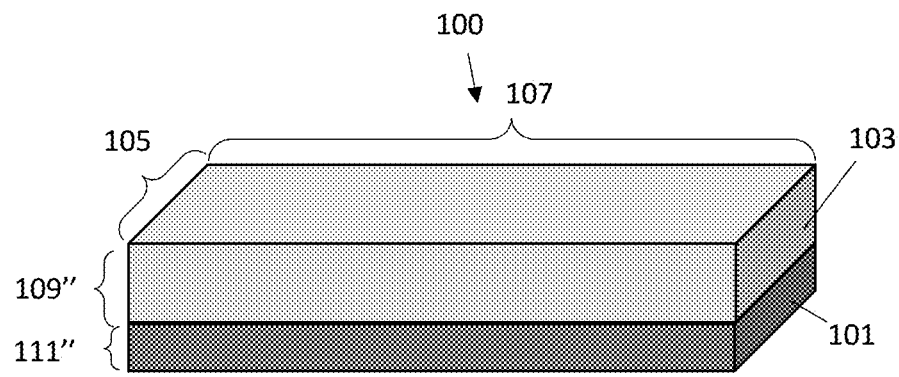
Figure 2D:
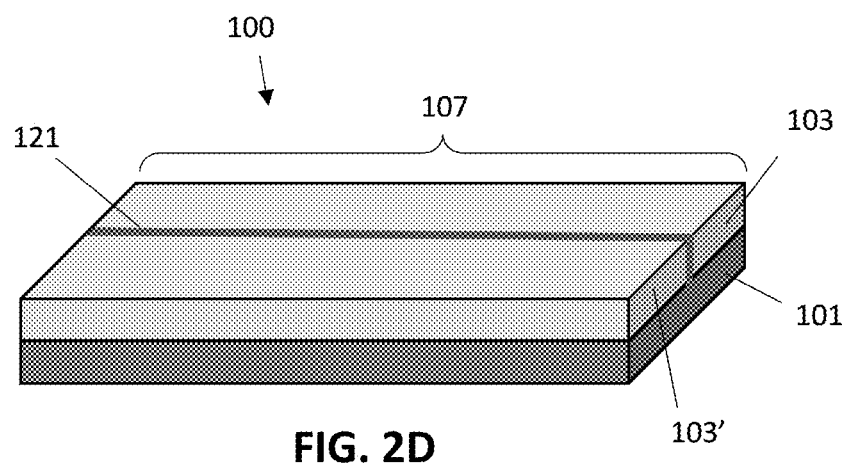

For example, as shown in FIGS. 1-2D, the biocompatible bone scaffold may be rectangular or approximately rectangular (e.g., rectanguloid), and may have one or more rounded edges. In some variations the scaffold has a structure dimensioned somewhat like a stick of gum, e.g., having a flat body that is longer than it is wide, and substantially thinner than it is wide or long. For example, the length and/or width may be greater than 2× (e.g., greater than about 3×, 4×, 5×, 10×, 15×, 20×, etc.) the thickness of the scaffold, where the thickness is the combined thickness of the mineralized and demineralized layers. The mineralized and demineralized layers may be the same length and width; in some variations the mineralized and demineralized layers have different lengths and/or widths but either the width and/or the length of the demineralized layer maybe within +/−20% (e.g., +/−18%, +/−15%, +/−12.5%, +/−10%, +/−8%, +/−7.5%, +/−5%, etc.) of the mineralized layer.

Thus, the scaffolds described herein typically comprise a collagen-based porous network capable of guiding tissue differentiation that can be used to regrow damaged soft tissues (e.g., connective tissue). The relatively high porosity, e.g. of either or both the demineralized and mineralized material may allow host integration, regeneration of relatively large sections of tissue, and vascularization. The collagen-based porous structure may allow binding of a variety of factors to the trabeculae (pores) within the scaffold formed of bone. Additional materials, such as hydrogels or extracellular matrix material, and/or a variety of biological components and therapeutic compounds may be integrated within the scaffold. The scaffolds may contain collagen trabeculae that may allow the structure to maintain a predefined shape and maintain nutrient transport. Thus, the scaffolds described herein may desirably provide mechanical integrity, nutrient transport during tissue regeneration, differentiation of well-defined cell populations, vascularization.

The grafts described herein may therefore include demineralized bone. The demineralized bone may be cancellous or corticocancellous bone. Cortical bone is the dense surface layer of the bone having little vascularization. In contrast, cancellous bone is a spongy material that makes up the bulk of the interior of bones. Compared to cortical bone it has a low density and strength, but very high surface area. These differences result in demineralized bone having differing properties, with demineralized cancellous bone comprising pores with diameters of about 100 microns to 2 mm while, in contrast, demineralized cortical bone may have a maximum pore size on the order of about 10 nm to 50 microns.

The term "biocompatible" may refer to any material having a relatively low risk of provoking an adverse response when introduced in a mammal, in particular a human patient. For example, a suitable biocompatible material when introduced into a human patient has relatively low immunogenicity and toxicity. The term "demineralized" may refer to bone from which a substantial portion of minerals natively associated with the bone minerals have been removed. The term "demineralized bone" is intended to refer to any bone, including cortical and/or cancellous bone, from any source including autologous, allogeneic and/or xenogeneic bone, that has been demineralized to contain, in certain embodiments, less than about 8 wt % residual calcium (e.g., less than about 7 wt % residual calcium, less than about 6 wt % residual calcium, less than about 5 wt % residual calcium, less than about 4 wt % residual calcium, less than about 3 wt % residual calcium, less than about 2 wt % residual calcium, or less than about 1 wt % residual calcium, etc.).

A scaffold is "substantially free of mineralized bone" when all of the bone within the scaffold has been exposed to demineralizing conditions and is at least partially demineralized. Scaffolds that are substantially free of mineralized bone are structurally and functionally distinct from bioscaffolds made from bone that has been masked prior to demineralization (see, e.g., US Published Application 20110066241).

The term "osteoconductive" may refer to the ability of a substance to support or conduct bone growth, while "osteoinductive" may refer to the ability of a substance to induce bone growth.

In some variations all or a portion of a scaffold as described herein may be comprised of demineralized cancellous bone and/or portions, regions, or segments of demineralized cancellous bone that have been stiffened by physicochemical methods, such as heating or stretching (i.e., strain hardening), or by crosslinking (e.g., chemically and/or physically) to increase their strength, e.g., to hold sutures, to aid in retention of shape, and/or to resist compression.

The bone scaffolds described herein may in certain embodiments be or include an autograft, an allograft or a xenograft. If the scaffold is a xenograft it may be from, by way of non-limiting example, ovine, porcine or bovine bone. The bone may be taken from any bone having suitable properties for the intended application of the scaffold. Properties to consider in selecting bone for the bioscaffold include porosity, pore size, connectivity, mechanical strength, surface area/volume ratio, the size of the scaffold required in the application, and the like. In some variations, as will be described below, the bone may include both regions of cancellous and cortical bone; thus the scaffolds may be derived from cortical and/or cancellous bone. In certain embodiments, the bone is vertebral, femoral, or pelvic cancellous bone. In certain embodiments, the scaffold may be made from a continuous piece of bone. In certain embodiments, the scaffold may be formed from multiple pieces of bone joined together, for example, by suturing, crosslinking, adhesively connecting, etc.

A bone material for use as a scaffold may be treated to remove cells (including marrow). The section of bone may then be shaped using methods known in the art. Alternatively, the bone may be shaped before removal of the marrow. The bone section may be shaped into any shape desired for the scaffold, particularly those described herein.

Bone may be demineralized in any appropriate manner. For example, demineralized bone may be formed by one or more of: decalcification by acid extraction; sonication in detergent solution (e.g., TERGAZYME®, Alconox, White Plains, N.Y.); alternated with rinsing in pure water (as would be understood by the skilled artisan, this cycle may be repeated as needed until substantially all fat, marrow, and other components in the trabecular space are removed); treatment with alkylammonium salts of EDTA, defatting by soaking in acetone;

treatment with hydrochloric acid (HCl), in certain embodiments with ethylene diamine tetraacetic acid (EDTA). In certain embodiments, the demineralization process may include treatment with one or more nonionic detergents, such as TRITON® X-100, Tween® 80, N,N-Dimethyldodecylamino-N-oxide, Octylglucoside, Polyoxyethylene (PEG) alcohols, Polyoxyethylene-p-t-octylphenol, Polyoxyethylene nonylphenol, Polyoxyethylene sorbitol esters, Polyoxy-propylene-polyoxyethylene esters, and p-isoOctylpolyoxy-ethylene-phenol formaldehyde polymer.

In certain embodiments, the bone scaffolds may be washed in peroxide (e.g., $H_2O_2$) to remove osteoinductive factors. Other methods and reagents for removing osteoinductive factors are known in the art, and include those described in U.S. Pub. 2005/0136124. Osteoinductivity of resulting scaffolds can be determined using standard methods in the art, such as ELISA for BMP or other factors that contribute to osteoinductive activity (e.g., fibroblast growth factor-2 (FGF-2), insulin-like growth factor-I and -II (IGF-I and IGF-II), platelet derived growth factor (PDGF), and transforming growth factor-beta 1 (TGF-β1)), on eluates during/after the treatment process.

One or more agents may be added to all or a portion of the scaffolds described herein. For example, in some variations the demineralized or mineralized layers (or both) may include an agent to enhance ingrowth and/or attachment to the connective tissue and/or the bone. In some embodiments, the bone scaffold (either or both the demineralized or mineralized layers) may be embedded with, injected with or otherwise have attached thereto, cells, any of a variety of pharmaceuticals, antibiotics, growth factors, hydrogel, collagen gel or mixtures thereof. It is contemplated that any composition, compound or biologic that helps in healing and integration of the scaffold may be added. Non-limiting examples of cells that may be added to a scaffold include any variety of stem cell, such as adult stem cells or cells derived from the soft tissue to be repaired (e.g., cells from soft tissue including tendon, ligament, fascia, fibrous tissues, fat, synovial membranes, cartilage tissue, meniscal tissue, ligament tissue, tendon tissue, and combinations thereof) or mixtures thereof. The tissue used can be autogeneic tissue, allogeneic tissue, or xenogeneic tissue. Tissue and/or cells can be obtained using any of a variety of conventional techniques, for example, by biopsy or other surgical removal. Preferably, the tissue sample is obtained under aseptic conditions.

Any of these scaffolds may have embedded therein, are embedded in, injected with, encapsulated by or otherwise attached to one or more polymeric carriers and/or matrices which may be adapted to contain and release a compound or cell type of interest. For example, in some variations the scaffold, and particularly the demineralized side, may be seeded with tendon progenitor cells. In certain embodiments, the carrier containing the compound is a combination with a carbohydrate, protein or polypeptide. Within certain embodiments, the polymeric carrier contains or comprises regions, pockets, or granules of one or more of the compounds. For example, within one embodiment, compounds may be incorporated within a matrix which contains the compound, followed by incorporation of the matrix within the polymeric carrier. A variety of matrices can be utilized in this regard, including for example, carbohydrates and polysaccharides such as starch, cellulose, dextran, methylcellulose, and hyaluronic acid, proteins or polypeptides such as albumin, collagen and gelatin.

In some variations, the scaffolds described herein include a biocompatible layer. Such biocompatible layers may be semipermeable or bioresorbable. In other embodiments, scaffolds may be embedded in or encapsulated by a biodegradable layer. Such biocompatible and/or biodegradable layers include biodegradable polymers. For example, in certain embodiments, poly(ϵ-caprolactone) (PCL) may be used with the scaffolds described herein. PCL is an aliphatic polyester which can be degraded by hydrolysis under physiological conditions and it is non-toxic and tissue compatible. The degradation of PCL is significantly slower than that of certain polymers and copolymers of lactic and glycolic acids and is therefore suitable for the design of long-term drug delivery systems. Other illustrative biodegradable polymers include, chitosan, heparin, chitosan-heparin complexes, biodegradable polymers, such as poly (DL-lactide-coglycolide) for sustained release delivery after implantation (Emerich, D F et al., 1999, *Cell Transplant*, 8, 47-58) or compositions comprising polybutylcyanoacrylate. In certain embodiments, bioresorbable polycaprolactone/polyglycolic acid (PCL/PGA) polymers are suitable. Examples of other biodegradable polymers include polymers or copolymers formed from monomers of lactide, glycolide, dioxanone, and caprolactone; collagen, fibrin, and silk; poly-(orthoesters) and poly-(anhydrides), polylactic acid, polyglycolic acid, copolymers of polylactic and polyglycolic acid (e.g., poly(lactic-co-glycolic acid; PLGA), polyepsilon caprolactone, polyhydroxy butyric acid, polyorthoesters, polyacetals, polydihydropyrans, polycyanoacrylates and cross linked or amphipathic block copolymers of hydrogels. As used herein, the term "glycolide" is understood to include polyglycolic acid. Further, the term "lactide" is understood to include L-lactide, D-lactide, blends thereof, and lactic acid polymers and copolymers. Biocompatible layers may be applied to the scaffold, by a variety of well-known techniques. For illustration, heparin can be applied to the scaffold in various ways including: First, benzalkonium heparin (BA-Hep) solution can be applied to the scaffold by dipping the scaffold in the solution and then air-drying it. This procedure treats the scaffold with an ionically bound BA-Hep complex. Second, EDC can be used to activate the heparin, then to covalently bond the heparin to the scaffold. Third, EDC can be used to activate the collagen, then covalently bond protamine to the collagen and then ionically bond heparin to the protamine. Many other coating, bonding, and attachment procedures are well known in the art and may also be used. Treatment of the scaffold with drugs in addition to or in substitution for heparin may be accomplished as described elsewhere herein and based on art-established techniques.

In some variations the scaffolds described herein may also or alternatively include radio opaque materials (e.g., barium sulfate) that will render the scaffolds radio opaque. The scaffolds may also include materials that will promote tissue regeneration or regrowth, as well as those that act as buffers, reinforcing materials or porosity modifiers. As mentioned, the bone scaffolds described herein may be embedded with or otherwise comprise any of a variety of biomolecules, growth factors, differentiation factors, and like biological components. Any agent that facilitates tissue repair is contemplated for use with the scaffolds described herein. The biological components used in the scaffolds can also be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED® and SURGICEL®, available from Ethicon, Inc.), hyaluronic acid, and compounds or agents that suppress the immune system (e.g., immunosuppressants). The component or effector compounds included with the scaffolds described herein can be incorporated within the scaffold before or after manufacture of the scaffold, or before or after the surgical placement of the scaffold. Prior to surgical placement, the biocompatible scaffold can be placed in a suitable container comprising the biological component. After an appropriate time and under suitable conditions, the scaffold will become impregnated with the biological component. Alternatively, the biological component can be incorporated within the scaffold by, for example, using an appropriately gauged syringe to inject the biological agent(s) into the scaffold. Other methods well known to those of ordinary skill in the art can be applied in order to load a scaffold with an appropriate biological component, such as mixing, pressing, spreading, centrifuging and placing the biological component into the scaffold. Alternatively, the biological component can be mixed with a gel-like carrier prior to injection into the scaffold. The gel-like carrier can be a biological or synthetic hydrogel as described elsewhere herein, and/or may include an alginate, a crosslinked alginate, hyaluronic acid, collagen gel, poly(N-isopropylacrylamide), poly(oxyalkylene), a copolymer of poly(ethylene oxide)-poly(propylene oxide), poly(vinyl alcohol) and blends thereof. In some variations, following surgical placement, an implant wherein the biocompatible scaffold is devoid of any biological component can be infused with biological agent(s), or an implant wherein the scaffold includes at least one biological component can be augmented with a supplemental quantity of the biological component. One method of incorporating a biological component within a surgically installed implant is by injection using an appropriately gauged syringe.

Further agents for use with the scaffolds described herein include any one or more of a variety of antibiotics. Antibiotics are well known in the art and include Abacavir, Acyclovir, Albendazole, Amikacin, Amoxicillin, Ampicillin, Azithromycin, Aztreonam, Benzilpenicillin, Cefepime, Ceftriaxone, Cephalexin, Chloramphenicol, Chloroquine, Cilastatin, Clindamycin, Co-trimoxazole, Didanosine, Dioxidine, Doxycycline, Famciclovir, fluoroquinolones, Fluconazole, Fosfomycin, Furazolidone, Fusidic acid, Ganciclovir, Gentamicin, Isoniazid, Josamycin, Kanamycin, Ketoconazole, Lamivudine, Lincomycin, Linezolid, Mebendazole, Meropenem, Metronidazole, Moxifloxacin, Mupirocin, Nystatin, Nitrofurantoin, Nitroxoline, Norfloxacin, Ofloxacin, Ornidazole, Oseltamivir, Polymixin B, Polymyxin M, Proguanil, Ribavirin, Rifampicin, Rimantadine, Roxithromycin, Spectinomycin, Sulfodimidin, Teicoplanin, Terbinafine, Tetracycline, Timidazole, Valaciclovir, Valganciclovir, Vancomycin, Zanamivir, and Zidovudine.

Further agents for use with the scaffolds described herein include any one or more of a variety of anti-viral drugs. Anti-viral drugs are well known in the art. Illustrative anti-viral agents include, but are not limited to Abacavir—anti-HIV. NRTI drug. "Ziagen" (ViiV Healthcare). In combination formulations: "Trizivir" and "Kivexa/Epzicom", Aciclovir—anti-HSV, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Immunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Stavudine, Synergistic enhancer (antiretroviral), Tea tree oil, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, and Zidovudine.

In further embodiments, the surface chemistry of the scaffold may be altered. In this regard, the surface may be modified by covalent (direct) attachment of biomolecules or by adsorption of biomolecules. Illustrative biomolecules include any of the biomolecules disclosed herein, such as but not limited to cellular proteins, any of the polymers described herein, collagens, extracellular matrix components, cytokines, growth factors, anti-inflammatory mediators and others.

In certain embodiments, the surface structure of the scaffold may be modified to provide texture, roughness and/or three-dimensional unevenness to the scaffold. The surface roughness of the scaffold may be altered by chemical etching or by physical etching. The scaffolds described herein may also be used as delivery devices for therapeutics, wherein the therapeutic comprises the minced tissue, which may include a combination of cells, extracellular matrix and/or inherent growth factors. The scaffold portion of the implant may thus permit hormones and proteins to be released into the surrounding environment.

The fully demineralized layer(s) of the scaffold may have a calcium content of, for example, from about 0% to about 2%. The scaffold may further comprise a partially demineralized bone layer between the mineralized segment and the demineralized bone segment. A partially demineralized bone segment may have a calcium content from about 2% to about 10% calcium. The partially demineralized segment may be significantly smaller than either the fully demineralized or the mineralized segments.

The bone scaffolds described herein may be used to repair of ligaments, tendons, cartilage or growth plates in the shoulder, hand, elbow, knee, foot, ankle or any other anatomical location as needed. Furthermore, the scaffold of the present invention may be applied to replace or repair any of a variety of joints.

The fully demineralized layer(s) of the bone scaffolds described herein may be formed by any appropriate method. In some variations the mineralized layer(s) may be masked before demineralization. Any method or substance may be used to mask the bone that is resistant to demineralization conditions and in some variations this masked region may be readily removed after demineralization. Alternatively, the bones may be masked with a material that is biologically and physiologically compatible and therefore does not need to be removed after demineralization. In some variations the layer to remain mineralized may be masked with wax or with a polymer. In one illustrative embodiment, the polymer is any polymer that may be removed with acetone or ethanol.

Masking may be particularly difficult to achieve precisely with the exacting thicknesses (and ratios of thicknesses, e.g., of mineralized to demineralized) described herein. Thus, in some variations more precise means be used, including in particular, starting with bone that includes both cortical and cancellous bone, as will be described in greater detail below.

As mentioned above, the scaffolds described herein may be treated to increase the strength of the scaffold. For collagenous structures, crosslinking provides greater mechanical strength and a degree of resistance to proteolytic enzyme degradation, increasing the in vivo lifetime of the cancellous bone scaffolds. The cancellous bone scaffolds may be crosslinked, either chemically or mechanically. Crosslinking the cancellous bone scaffold may substantially increase the mechanical integrity of the scaffold, without substantially altering the cytocompatibility of the scaffold. Additionally, both the physical and chemical crosslinking methods may be biologically compatible. Non-limiting examples of physical crosslinking may be dehydrothermal crosslinking or crosslinking by exposure to gamma radiation or ultraviolet radiation. Physical crosslinking methods of proteinaceous material such as the cancellous bone scaffolds are well known in the art. Alternatively or additionally, the bone scaffold may be chemically crosslinked. Functional groups that specifically react with amines may be, but not limited to, aldehydes, N-hydroxysuccinimide (NHS), isocyanate, epoxide and acrylate. The collagen material of the cancellous bone scaffold is known to comprise lysine residues that may be crosslinked. Functional groups that are non-selective may be, but not limited to, active esters, epoxides, azides, carbonylimidazole, nitrophenyl carbonates, tresylate, mesylate, tosylate and isocyanate. Other agents may also be employed for chemically crosslinking the cancellous bone scaffold, including, but not limited to, carbodiimides, genipin, aldehydes such as glutaraldehyde and formaldehyde, acyl azide, poly-epoxy compounds, butanediol diglycidyl ether, dye mediated photooxidation or tannic acid. A mixture of crosslinking agents may be used. The choice of crosslinking agent may depend on the amount of crosslinking desired, although this may also be controlled by controlling the time of the crosslinking reaction and/or by controlling the concentration of the crosslinking agent.

In some variations, the osteoinductivity of the scaffold (and particularly the demineralized layer) may be removed from the cancellous bone scaffold, e.g., using peroxide or other agents, as described above.

The scaffold described herein may be useful in treating injuries involving interfaces within connective tissues. The major applications include repair of ligaments, tendons, and cartilage. Ligaments are dense bands of connective tissue composed primarily of type I collagen that connect bones to other bones. Ligaments function as motion guides and joint motion restrictors. At all articulating joints (neck, spine, shoulder, elbow, wrist, hip, knee, ankle) in the body, these tissues are placed under constant dynamic loading. An injury known as a sprain results when the ligaments are stretched, and in some cases, stretched severely enough to be torn. While in some cases, ligament tears can heal on their own, other cases show a lack of inherent healing capacity. If left untreated or if treated improperly, ligament tears can lead to chronic disability including arthritis at the affected joint. Tendons, like ligaments, are dense collagenous tissues found at every articulating joint in the body. Tendons, however, connect muscles to bone, allowing the force produced by the muscles to be translated into motion. When overloaded, tendons are at risk for tearing and in some cases require surgical replacement to return joint motion and prevent muscle atrophy.

FIGS. 2A-2D illustrate examples of grafts as described herein including a mineralized layer 103 and a demineralized layer 101. As mentioned above, in some variations the scaffold may have dimensions that are optimized to prevent breaking, improve delivery and enhance integration into the tissues of the body. For example, in some variations the scaffold 100 may be configured as rectanguloid body having dimensions in which the length 107 is between about 15 and 50 mm (e.g., between 15-35 mm, between 15-30 mm, between 20-30 mm, between 20-28 mm, between 15-25 mm, etc.), the width 105 is between about 10-26 mm (e.g., between 12-18 mm, between 15-20 mm, between 10-15 mm, between 13-17 mm, etc.), and the thickness is between 2-6.5 mm (e.g., between 2-6.0 mm, between 2-5.5 mm, etc.).

The thickness of the demineralized 111 and mineralized 109 layers may be different. For example, as shown in FIG. 2B, the demineralized layer 111' is thicker (e.g., between 60-99% of the thickness of the body of the scaffold, e.g., between 60-95%, between 65-99%, between 70-95%, etc.). The thickness of the mineralized layer 109' may be, e.g., between about 40 and 1% of the thickness of the body (e.g., between 35-1%, between 35-1%, between 35-5%, etc.). In particular, the thickness of the mineralized layer may be limited to a maximum (regardless of the thickness of the demineralized layer), such as about 1.5 mm or less (e.g., 1.4 mm or less, 1.3 mm or less, 1.2 mm or less, 1.1 mm or less, 1.0 mm or less, 0.9 mm or less, 0.8 mm or less, 0.7 mm or less, between about 1.4 mm and 0.1 mm, between about 1 mm and 0.1 mm, etc.)

Alternatively, in some variations, as shown in FIG. 2C the mineralized layer 109" is thicker (e.g., between 60-90% of the thickness of the body of the scaffold, e.g., between 60-85%, between 65-85%, between 70-80%, etc.). The thickness of the demineralized layer 111" may be, e.g., between about 40 and 10% of the thickness of the body (e.g., between 40-15%, between 35-10%, between 35-15%, etc.).

In some variations the graft may be configured for insertion into the body. For example, the graft may include a thin mineralized bone layer formed adjacent to a thicker demineralized layer to provide bending without breaking the mineralized layer.

Figure 2E:
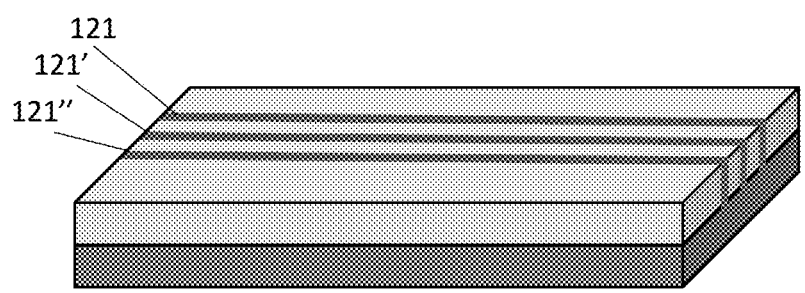

In some variations, the graft may include regions of fully demineralized bone. FIG. 2D illustrates one example of a scaffold including regions between mineralized layer regions formed by demineralizing the bone in these regions. These regions may be one continuous region (e.g., a longitudinally-extending region, etc.) or a plurality of separate regions. In FIG. 2D, the scaffold 100 includes a central longitudinal region 121 through the mineralized layer (the longitudinal axis may be referred to as the long axis, and may line in the direction of the length 107 of the scaffold). The demineralized bending region may provide sufficient flexibility so that the mineralized bone layer 103, 103' on either side of the region may flex or bend for inserting into a cannula to be delivered into the body. FIG. 2E shows another example of a scaffold implant that includes a plurality of demineralized regions formed along the length of the mineralized bone layer 103. The demineralized regions (bending regions) may extend completely to the demineralized layer 101 or partially to the demineralized layer.

In some variations the scaffold may be notched to allow it to bend, e.g., by notching the mineralized side (not shown). This may be done in addition to or instead of including a region of demineralized bone.

Figure 3:
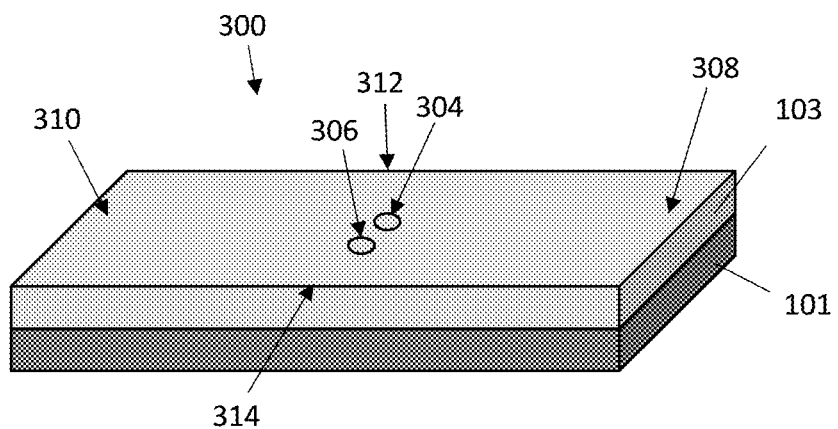
FIG. 3 is an example of a bone scaffold including pre-formed suture channels.

Any of the scaffolds described herein may include one or more channels or openings configured to receive suture for attaching the device to the body and/or for attaching the tissue (connective tissue) to the scaffold. In particular, the openings or channels may be suture channels that may extend in some variations transversely through the thickness, as shown in FIG. 3A. In FIG. 3 two suture channels 304, 305 are shown through the middle region of the scaffold 300; these channels may pass completely through the mineralized layer 103 and in some cases through the demineralized layer 101. Alternatively in some variations a suture channel may extend just partially into the thickness and then travel transversely (not shown) and then exit the same side it entered from or a different side.

In any of these variations the suture channel may be treated to prevent snagging, treating or breaking the suture (e.g., on the porous structure of the bone) or risk damaging the bone. For example, the bone regions forming the channel may be compressed, polished, and/or sealed to prevent access to the trabecula within the layer(s). In some variations the opening into the scaffold may be rounded to remove any sharp edges.

Any number (e.g., 1, 2, 3, 4, 5, 6, 7, 8, etc.) of openings into the bone layers may be formed in the scaffold. The positions of the one or more openings may be arranged in any appropriate region of the scaffold, such sat the central region, an upper region 308, a lower region 310, a right side region 312 or a left side region 314, and/or any combination of these. In some variation the scaffolds may be pre-threaded with one or more sutures through the suture openings, and provided the user (e.g. doctor) for implantation.

Figure 4A:
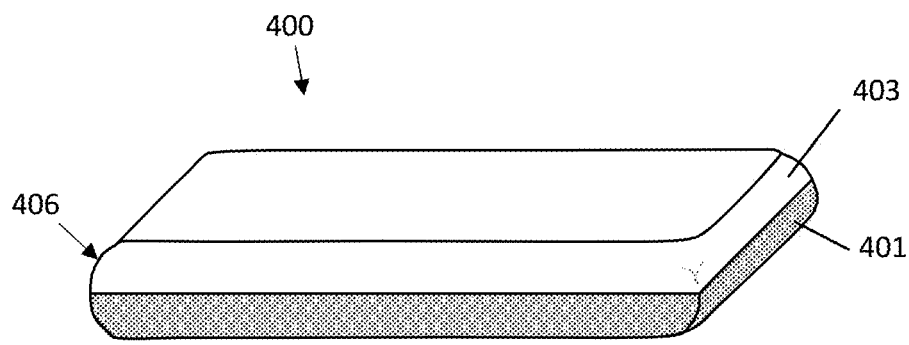
FIGS. 4A-4B illustrate bone scaffolds having rounded (FIG. 4A) or tapered (FIG. 4B) edges as described herein.
Figure 4B:
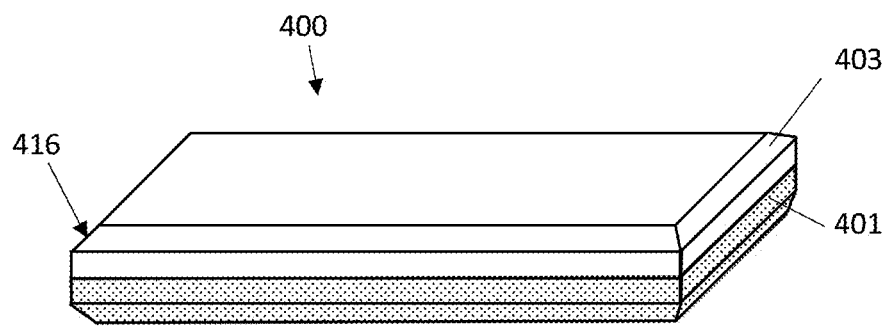

Any of the scaffolds described herein may include rounded or beveled edges. For example, a scaffold may include edges (outer edges of the body) that are rounded, e.g., having a radius of curvature of between about 0.1 mm and 2 mm (e.g., between about 0.2 and 2 mm, between about 0.3 and 2 mm, between about 0.1 and 1.5 mm, between 0.1 about 1 mm). For example, FIG. 4A shows one example of a scaffold having rounded edges. FIG. 4B is an example of a scaffold having tapered edges. In FIG. 4A, the rounded edges 406 extend around the perimeter of the scaffold, on both the demineralized 101 and mineralized 103 layers of the scaffold, which may prevent trauma to the tissue into which the scaffold is inserted. In some variations just the demineralized (e.g., outward-facing) portion of the scaffold includes rounded and/or tapered edges. FIG. 4B shows a variation of a scaffold 400 including tapered edges 416.

In some variations the scaffold may be formed of a single portion of a bone that is treated to form the demineralized and mineralized layers in an arrangement as described herein. In some variations the scaffold layers may be separately formed and combined either before or during insertion into the patient's body. For example, in some variations the demineralized layer may be formed as a single layer that is mated with the mineralized layer. The demineralized layer may be attached (affixed) to the mineralized layer. For example the mineralized and demineralized layers may be chemically, mechanically, thermally or otherwise bonded together. For example in some variations a chemical adhesive may be used to bond the demineralized and mineralized layers together. In some variations the mineralized and demineralized layers may be shaped to interlock of engage in a predefined manner. For example the demineralized layer may include a projection into which the mineralized layer inserts, or vice versa (or both).

Figure 5A:
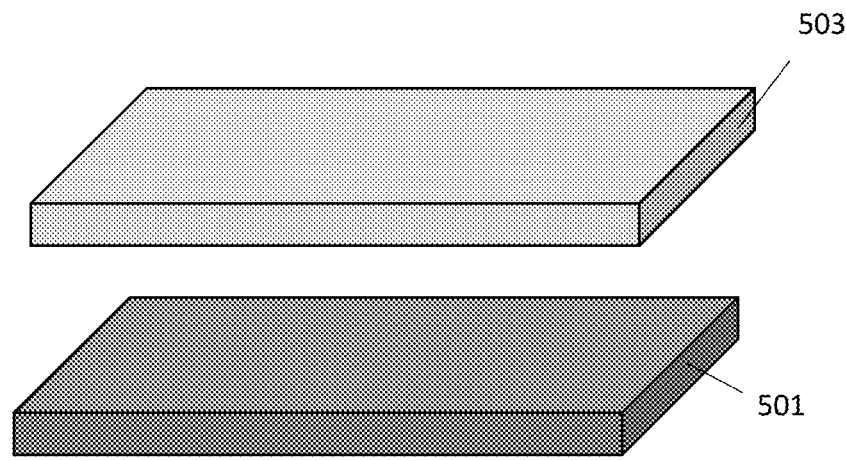
FIGS. 5A-5B show examples of bone scaffolds having initially separate demineralized and mineralized layers.
Figure 5B:
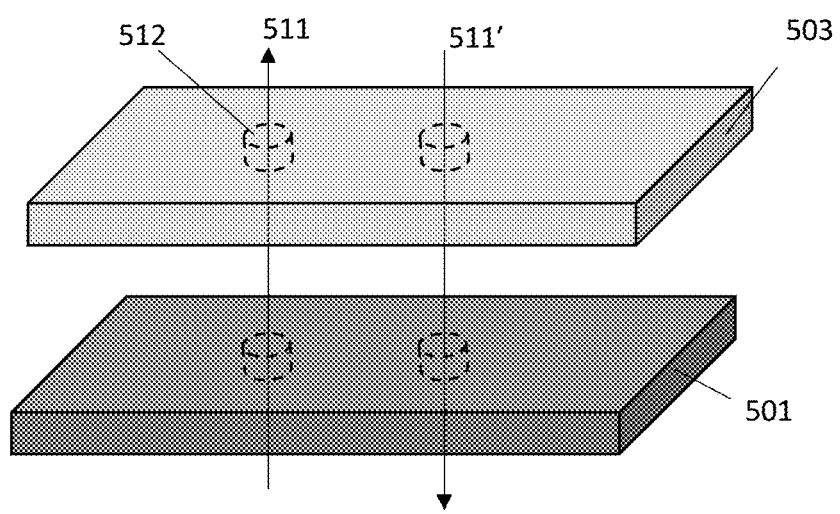

FIG. 5A illustrates one example of a scaffold formed of initially separate demineralized 501 and mineralized 503 layers. In FIG. 5B, the initially separate layers may be coupled together by a suture 511 or sutures 511', that may pass through pre-formed suture openings or passages 512. Thus, the suture may be used to affix the two (or more) layers together during a procedure to insert/apply them. The different layers may be formed of different regions of bone and/or different regions of the same or different bone types (e.g., cancellous and cortical, etc.).

Also described herein are scaffolds that are cancellous and cortical bone scaffolds.

For example, a section of bone comprising both cancellous and cortical bone regions may be used as a starting material that may be treated to demineralize the bone. The demineralization rate and required conditions for demineralization of cancellous and cortical bone are different. At multiple points in the body (i.e. the head of long bones) there is are cortical cancellous interfaces. Such interfaces may be used to form cortical and cancellous scaffolds from a single allograft material (e.g., without requiring a lamination step, such as shown in FIGS. 5A-5B) or other attachment of two disparate bone types. The pore structure of cancellous bone material may allow for better penetration of the demineralization solution and an overall higher surface area to volume ratio enabling the demineralization of this portion of the bone more effectively. This change in porosity and resistance to demineralization could be used in allograft material to form a scaffold with a mineralized side and a demineralized side. For example, the whole bone may be placed in a demineralization solution for an amount of time sufficient to render the cancellous side to the appropriate level of demineralization (e.g., <8% Calcium, <7% Calcium, <6% Calcium, <5% Calcium, <4% calcium, <3% calcium, <2% calcium, etc.). The bone scaffold may then be placed with the cancellous side in demineralization solution and the cortical side above the level of solution. The reduced porosity of the cortical bone may prevent the demineralization solution from wicking through the bone as it does in cancellous bone. Either before or after the demineralization, the bone material may be trimmed or cute to the appropriate dimensions as described herein.

The resulting implant may therefore be a scaffold having a first layer that is formed of a demineralized cortical bone that is immediately adjacent (and in some variations contiguous with, e.g., formed of a unitary structure) a mineralized cortical layer of bone.

Any of the implants described herein may be hydrated or non-hydrated, for storage prior to use. Before implantation into the body, they maybe hydrated, e.g., by soaking or adding a fluid, e.g., water, saline, buffer, protein solution (such as platelet-rich plasma, PRP), etc.

Thus, any of the scaffolds described herein may include a trapezoidal (e.g., rectanguloid) body that may be, e.g., wider on a superior side, narrower on an inferior side. Alternatively, in some variations the scaffold may be oval shaped (or may have an oval cross-section, e.g., having rounded edges). The scaffold may be formed of any appropriate source of bone (e.g., cancellous, cortical, both cancellous and cortical, etc.) from any appropriate region (e.g., pelvis, etc.). The density of the bone may be different between the mineralized and demineralized regions/layers; thus the size and/or number of trabeculae/porosity may be different between the mineralized and demineralized bone layers.

In some variations all or some of the surfaces of the mineralized and/or demineralized layers may be grooved or textured. For example, just the inferior side may be grooved or just the superior surface of both mineralized and demineralized or just mineralized or just demineralized layers. Other textures may be used, including grids, parallel channels, etc.

As mentioned above, any appropriate method of making the scaffold may be used, including creating separate mineralized and demineralized layers using wicking (e.g., pressure-limited or driven wicking) to predetermined and precisely controlled thicknesses. One or more masking agents may be used, including masking agents having selected viscosities or densities, and/or controlling temperature (decrease temperature or increase temperature) of the masking agent and/or demineralizing solution to control the depth of demineralization compared to the remaining mineralized layer.

The scaffolds described herein may be sterilized and may be configured for sterilization. For example, these scaffolds may be sterilized by gamma sterilization, e-beam sterilization, supercritical carbon dioxide sterilization, etc.

In use, these scaffolds may be implanted into a patient in need thereof in any appropriate technique. In particular, these scaffolds may be implanted via an arthroscopic procedure, a mini-open procedure, etc. As mentioned, the scaffold may be configured for insertion to the body via a cannula, and may be affixed via a suture. In some variations the scaffold may be used to repair tendon tears on the articular surface; in some variations the scaffold may be used to repair tendon tears on the bursal surface.

Figure 6:
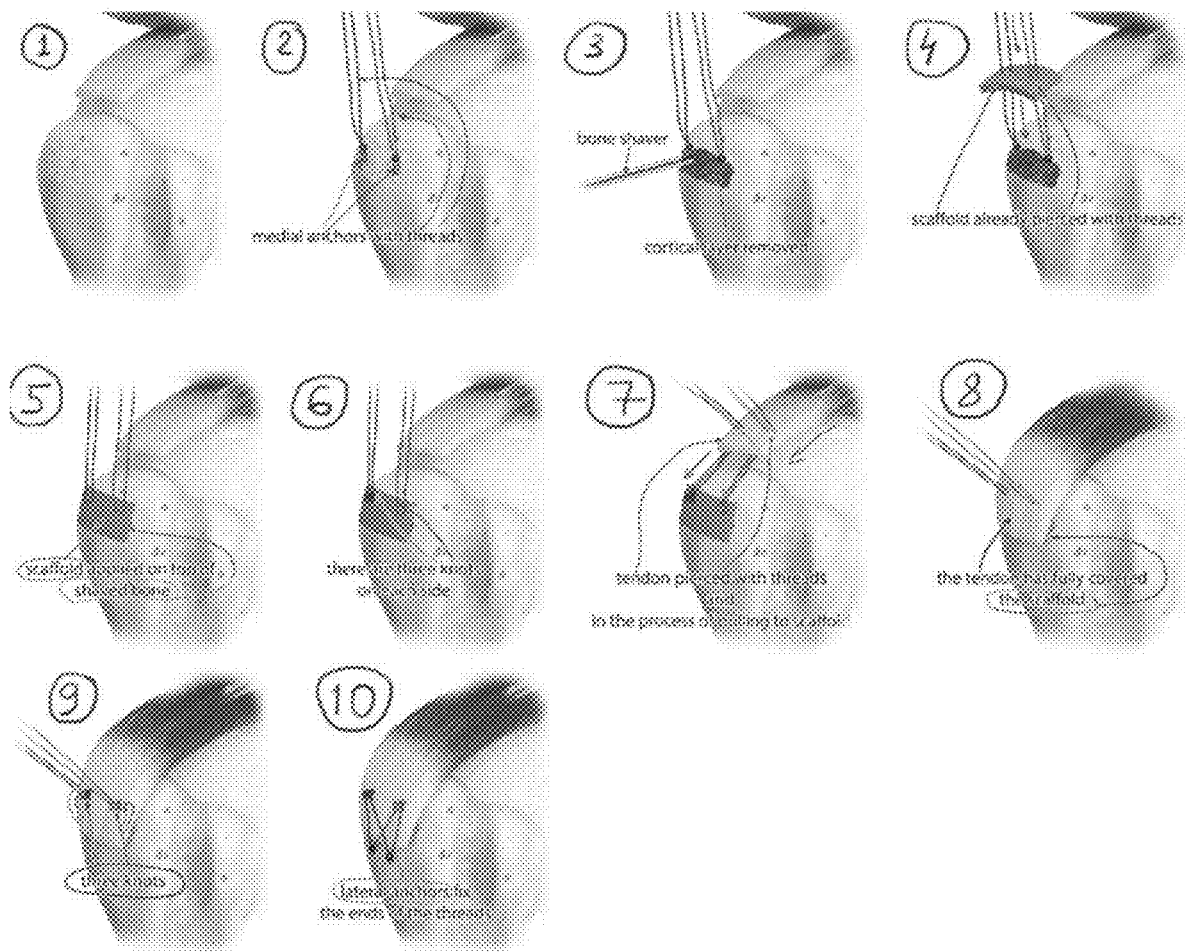
FIGS. 6(1)-6(10) illustrates one method of implanting/inserting bone scaffold to repair a connective (e.g., tendon) tissue as described herein.

Any appropriate tissue may be repaired, including, but not limited to rotator cuff tissue. For example, FIG. 6 illustrate one method of using a scaffold as described herein to repair a rotator cuff. In FIG. 6(1), the tissue to be repaired may be prepared, e.g., by removing unwanted tissue and/or debriding. In FIG. 6(2), the boney region to which the scaffold will be anchored is prepared, by applying one or more anchors (e.g., medial anchors) including sutures ("threads"). A bone shaver may be used to cut away the region into which the scaffold will be applied, as shown in FIG. 6(3). The mineralized side may be placed down onto the exposed inner bone region, so that the marrow may be driven, e.g., by pressure, into the trabecula of the mineralized bone helping to vascularize the scaffold to the native bone tissue. In FIG. 6(4), the scaffold (which may be preloaded on the sutures, e.g., via one or more suture channels, as described above, may be slid down through a cannula (not shown) and into the bone. In FIG. 6(5), the scaffold is applied onto the prepared bone and may be anchored, via the suture, in place, as shown in FIG. 6(6). In FIG. 6(7), the tendon to be repaired may be sutured with the same sutures used to anchor the scaffold (or coupled to the scaffold anchors) and may be pulled down onto the scaffold outer surface (e.g., the demineralized layer of the scaffold). FIG. 6(8) shows the tendon fully covering the scaffold, and in FIG. 6(9) and FIG. 6(10) the sutures may be used to anchor and secure the tendon to the scaffold. In some variations additional material may be used to secure the tendon to the scaffold. In some variations, no additional securement or augmentation is not necessary.

Stiffness

As mentioned above the implants (e.g., grafts) described herein may be configured to be sufficiently flexible so that they may be inserted through a cannula without requiring a specific hinge region. For example, any of the bone scaffold grafts described herein may be configured so that they may be bent (e.g., folded, curled, etc.) without breaking or cracking. This may be achieved, at least in part, by controlling the overall thickness of the mineralized portion, and/or the relative thickness of the mineralized vs. the demineralize layers. For example, the bone scaffold grafts described herein may have an overall graft thickness that is limited to between 4.5-6.5 mm thick or less (e.g., 6.5 mm or less, 6.0 mm or less, 5.5 mm or less, 5.4 mm or less, 5.3 mm or less, 5.2 mm or less, 5.1 mm or less, 5.0 mm or less, 4.9 mm or less, 4.8 m or less, 4.7 mm or less, 4.6 mm or less, 4.5 mm or less, etc.) in which the maxim thickness of the mineralized portion is about 1.5 mm or less (e.g., 1.4 mm or less, 1.3 mm or less, 1.2 mm or less, 1.15 mm or less, 1.1 mm or less, 1.05 mm or less, 1.0 mm or less, 0.95 mm or less, 0.9 mm or less, 0.8 mm or less, etc. between about 100 µm and 1.25 mm, between about 100 µm and 1.1 mm, between about 150 µm and 1.1 mm, between about 150 µm and 1.0 mm, etc.).

Surprisingly, for bone scaffold grafts as described herein, in which the graft is formed of adjacent mineralized/demineralized layers in which the mineralized layers is about 1.5 mm or less, typically where the thickness of the bone scaffold grafts is between about 4.5 and 6.5 mm thick, the bone scaffold grafts is sufficiently flexible that, when hydrated, it may be easily bent without breaking. For example, the stiffness of bending a sheet-like bone scaffold graft (e.g., a graft formed into a planar sheet in which one side is the mineralized layer and the other is the demineralized layer) may have a stiffness, when measured as mean bending stiffness, that may be less than about 1 millinewtons meters (mNm) (e.g., less than about 1.2 mNm, less than about 1.1 mNm, less than about 0.9 mNm, less than about 0.85 mNm, less than about 0.8 mNm, less than about 0.75 mNm, less than about 0.7 mNm, less than about 0.65 mNm, less than about 0.5 mNm, less than about 0.25 mNm, less than about 0.1 mNm, etc.). Bone scaffold grafts having a thickness of the mineralized layer that is greater than 1.5 mm typically have a mean bending stiffness that is greater than this, and may be difficult to bend without cracking, breaking or otherwise damaging the bone scaffold graft.

Thus, described herein are bone scaffold grafts that have a maximum thickness that is about 1.5 mm or less (e.g., 1.4 mm or less, 1.3 mm or less, 1.2 mm or less, 1.15 mm or less, 1.1 mm or less, 1.05 mm or less, 1.0 mm or less, etc.). As mentioned, the overall thickness of the graft may be, e.g., between about 4.5 and 6.5 mm or less, with the majority of the thickness of the graft being formed of demineralized bone material. For example, the demineralized layer may be greater than 65% of the thickness of the bone scaffold graft (e.g., greater than 67%, greater than 70%, greater than 75%, greater than 80%, greater than 85%, etc.). These highly flexible bone scaffold graft implants described herein having greater than 60% or more of the thickness being demineralized bone (and having a maximum mineralized layer thickness of 1.5 mm or less, e.g., 1.4 mm or less, etc.) may also be easier to cut, without cracking or damaging the graft, than implants having higher thicknesses of the mineralized layer. Cutting to size may be important for implanting the graft material into the patient, as this may allow customization of the insertion/implantation site.

In addition to the enhanced flexibility, e.g., low mean bending stiffness of less than about 1 mNm, which may allow the bone scaffold grafts described herein (e.g., having a maximum thickness of the mineralized layer of about 1.5 mm of less) to be easily bent and cut to shape/size, any of the bone scaffold grafts described herein may also be optimized for conformability, allowing the graft material to conform to a potentially irregular surface, such as the prepared bone surface onto which the implant is to be applied. The prepared surface may be flat or uneven (e.g., not flat). Outcomes are expected to be far better if the bone scaffold graft sits flush against the bone onto which it is being grafted, even when the bone surface is curved or irregular. Traditional, more rigid or stiffer bone scaffold grafts are not capable of being applied flush against such uneven surfaces. Typically, the bone scaffold grafts described herein may be highly conformable.

This conformability may be a function of both the high flexibility described above, as well as a relatively high compressibility of the bone scaffold grafts described herein. For example, the bone scaffold grafts described herein, formed as adjacent sheets of mineralized/demineralized material, may be relatively highly compressible as a function of the thickness of the demineralized portion and/or the porosity of the graft material, particularly the porosity of the demineralized layer. The hydrated graft, ready for implantation, may be both highly conformable, as described above, and highly compressible, particularly where greater than 60% (e.g., greater than 65%, greater than 70%, greater than 75%, greater than 80%, greater than 85%, etc.) of the thickness of the graft is demineralized. In some variations a graft having greater than 66% (e.g., greater than 67%, greater than 70%, greater than 75%, greater than 80%, greater than 85%, etc.) of the thickness being formed of demineralized bone material, with an uncompressed thickness of between about 6.5 and 4.5 mm, may be compressed to a thickness of about 2 mm or less, when a force normal to the layer(s) is applied.

As mentioned above, the porosity of the bone scaffold grafts may be selected so that these grafts have a compressibility and/or flexibility (e.g., stiffness) as described. For example, the material used to form the bone scaffold grafts described herein may be selected to have a porosity so that the density of the material (where density may be a proxy for the porosity) is less than about $3.0e{-}4$ $g/mm^3$ (e.g., about $2.9e{-}4$ $g/mm^3$ or less, about $2.8e{-}4$ $g/mm^3$ or less, about $2.7e{-}4$ $g/mm^3$ or less, about $2.6e{-}4$ $g/mm^3$ or less, about $2.5e{-}4$ $g/mm^3$ or less, $2.4e{-}4$ $g/mm^3$ or less, $2.3{-}4$ $g/mm^3$ or less, $2.2e{-}4$ $g/mm^3$ or less, $2.1e{-}4$ $g/mm^3$ or less, $2.0e{-}4$ $g/mm^3$ or less, $1.9e{-}4$ $g/mm^3$ or less, etc.). In particular, the density may be $2.5e{-}4$ $g/mm^3$ or less (e.g., 0.00025 $g/mm^3$ or less). This density may be maintained by the mineralized region and approximately by the demineralized region, following formation. This range of porosity may also be important, in combination with the thickness of the mineralized region described above, for achieving the highly flexible grafts (e.g., low mean bending stiffness) grafts described herein. In some variations the porosity may also be substantially homogeneous.

Also described herein are bone scaffold grafts having a higher stiffness than those described herein, but in which the dimensions are narrower/smaller (e.g., having length and/or width dimensions that are 10 mm or less (e.g., 8 mm or less, 7 mm or less, 6 mm or less, 5 mm or less, etc.). Smaller bone scaffold grafts (e.g., having at least two dimensions (e.g., width and thickness) that are less than x mm (e.g., where x is 10 mm, 9 mm, 8 mm, 7 mm, 6 mm, 5 mm, 4 mm, etc.) may be stiffer than those described herein. However, in some variations, smaller bone scaffold grafts may have the mean bending stiffness, compressibility and porosity as described above (e.g., a mean bending stiffness of 1 mNm or less, a density of less than $2.6e{-}4$ $g/mm^3$, etc.)

In general, the bone scaffold grafts described herein may be provided in any length and width, and may be cut down for implantation by the physician. For example, the bone scaffold grafts may have dimensions (length×width) of between 50-10 mm by 80-20 mm, e.g., 25 mm×50 mm.

The thickness of the mineralized layer of bone scaffold graft may vary by less than +/−10% (e.g., less than +/−9%, less than +/−8%, less than +/−7%, less than +/−6%, less than +/−5%, less than +/−4%, less than +/−3%, less than +/−2%, less than +/−1%, etc.). This high level of uniformity in the thickness of the mineralized (and conversely the demineralized) layer(s) may provide uniformity in the key properties, such as stiffness, compressibility and compliance, discussed above, which may not otherwise be possible.

The bone scaffold grafts described herein may also or additionally advantageously be free of blood proteins. As described above, grafts may be provided dehydrated and may be rehydrated prior to use. The grafts may be rehydrated prior to cutting down to size before implantation.

Figure 7A:
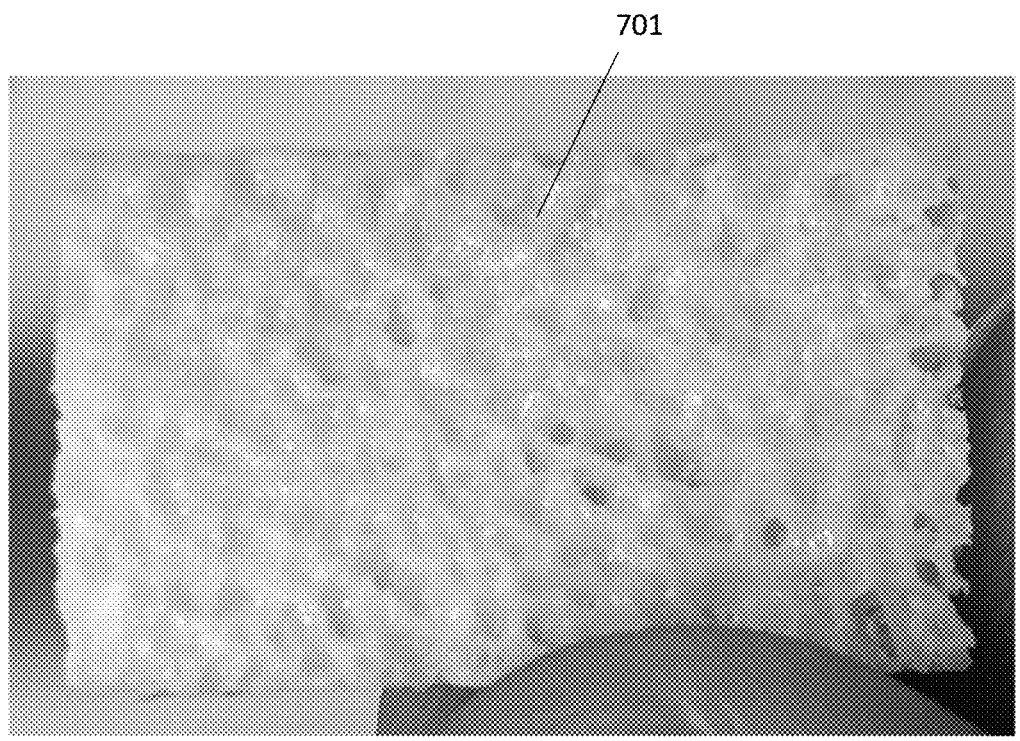
FIGS. 7A and 7B illustrate examples of the decalcified (FIG. 7A) and calcified (FIG. 7B) sides of a graft as described herein.
Figure 7B:
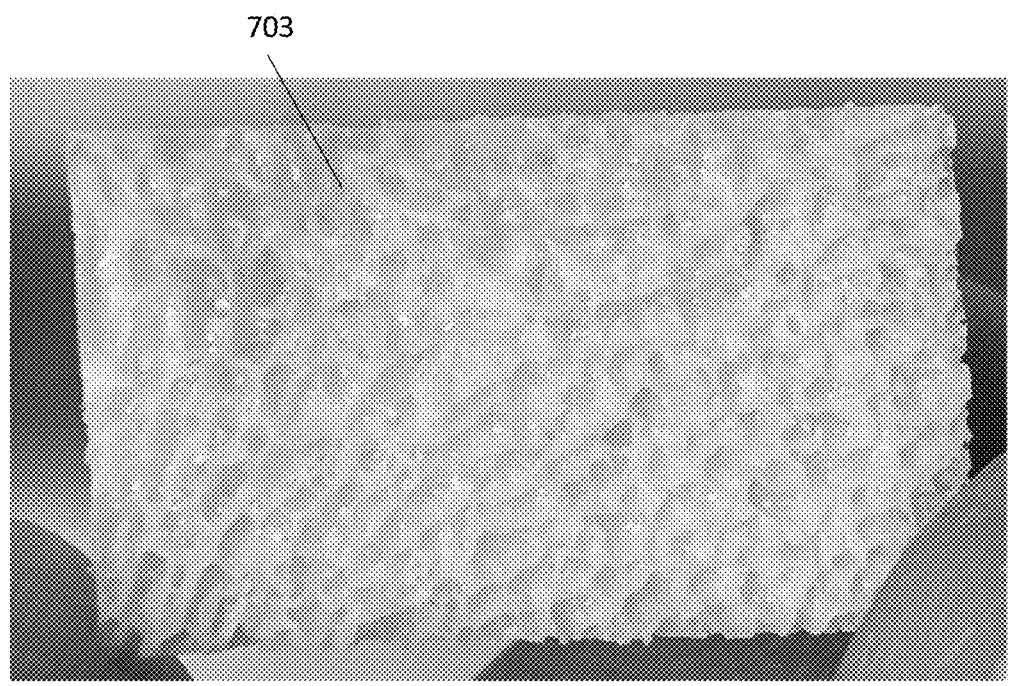
Figure 7C:
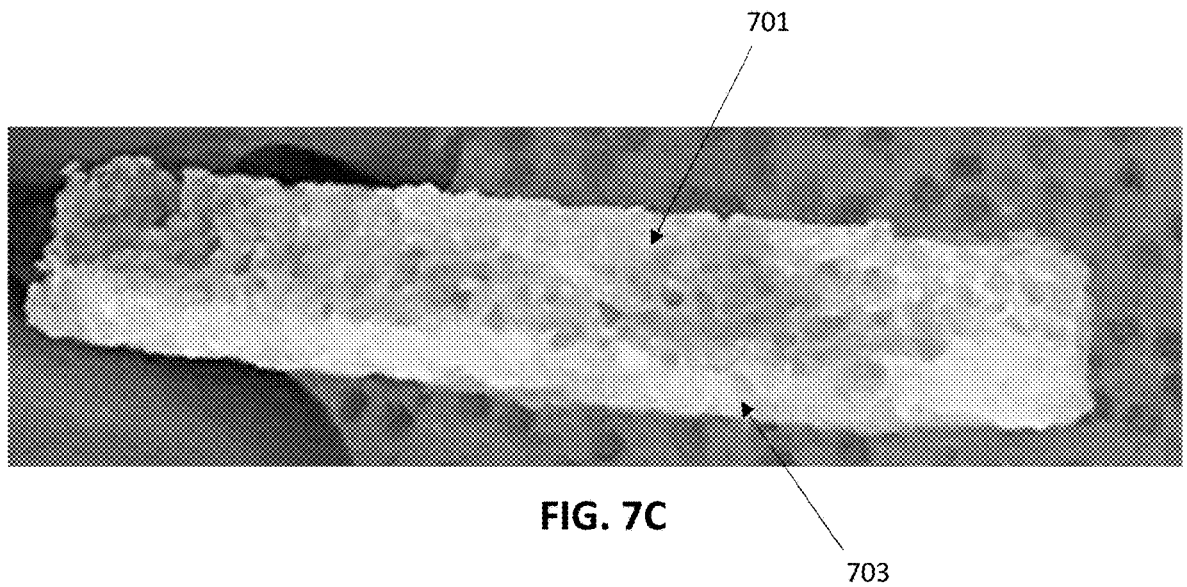
FIG. 7C shows a side view of a graft as described herein, including both calcified and decalcified layers, positioned adjacent to each other.

FIGS. 7A-7C illustrate examples of grafts as described herein. Each graft shown is approximately 25 mm by 15 mm and is formed from cancellous bone. In FIG. 7A the demineralized side 701 of the graft is shown. FIG. 7B shows a mineralized side 703 of the graft. FIG. 7C shows a side view of a graft such as the one shown in FIG. 7A, showing the mineralized layer 703 immediately adjacent to the demineralized layer 701. As described above, the mineralized layer is less than about 1 mm in this example. In FIG. 7C the thickness of the graft is approximately 4.5, and the thickness of the calcified region is approximately 1.5 mm. This graft is flexible and compressible, as described herein (not shown).

Figure 7D:
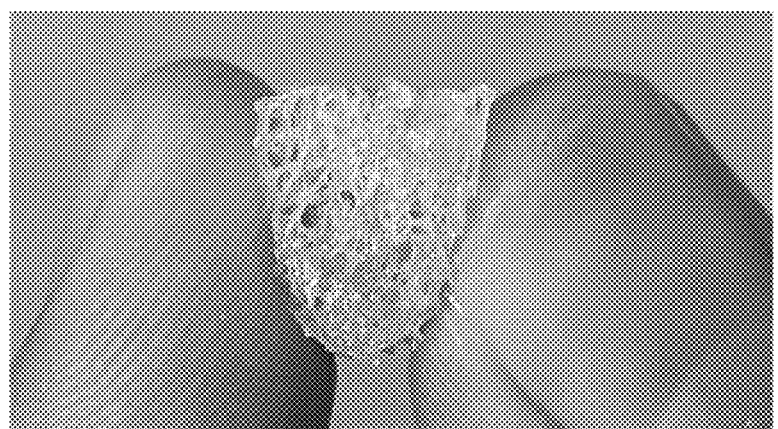
FIG. 7D shows an example of a graft (such as the one shown in FIG. 7C) being bent between two fingers.
Figure 7E:
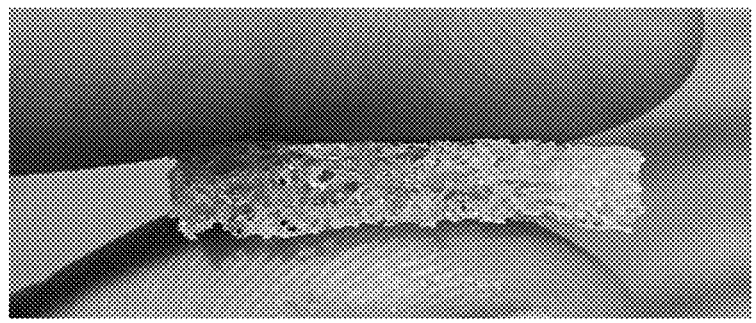
FIGS. 7E and 7F illustrate the compressibility of the graft shown in FIG. 7D.
Figure 7F:
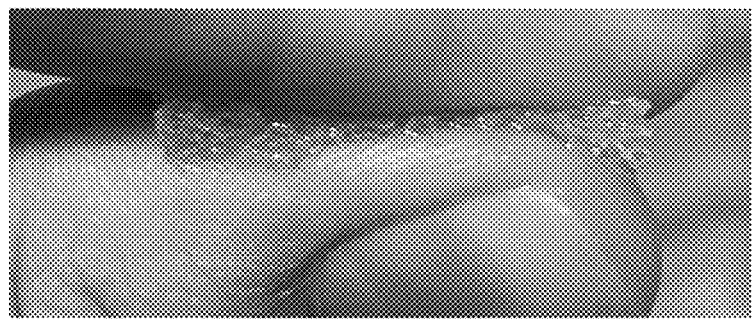

FIG. 7D illustrates the flexibility of the graft shown in FIG. 7C. IN this example the graft has been folded over itself completely, as shown. The graft, including in particular the mineralized layer, does not crack or become damaged despite bending relatively easily, and will return to its original flat shape following release of the bending force. Similarly, the same graft is also compressible and conforms to the surfaces applying the compression, as shown in FIGS. 7E and 7F. In this example the graft is shown held between two fingers (FIG. 7E) and is further shown compressed between these two fingers in FIG. 7F.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A flexible, compressible and compliant graft, the graft comprising a strip of bone forming a body having a length, a width and a thickness, wherein the thickness is between 4 mm and 6.5 mm and is less than half the length and half the width, the body further comprising:
   a first layer of porous demineralized bone extending the length and width of the body; and
   a second layer of porous mineralized bone extending along an outer surface of the strip that is continuously adjacent to the first layer, wherein the second layer has a constant thickness that is less than 1.5 mm;
   wherein the body has a density that is less than 2.6e-4 g/mm$^3$.

2. The graft of claim 1, wherein the second layer is between 1.2 mm and 0.1 mm thick.

3. The graft of claim 1, wherein the body has a mean bending thickness that is less than about 1.2 mNm.

4. The graft of claim 1, further comprising one or more suture channels pre-formed through the thickness of the body.

5. The graft of claim 1, wherein the edges of the body are rounded, having a radius of curvature of between 0.25 mm and 2 mm.

6. The graft of claim 1, wherein the edges of the body are beveled at an angle of between 30 and 60 degrees.

7. The graft of claim 1, wherein the first layer has a different color than the second layer.

8. The graft of claim 1, wherein the body has a length of between 15 and 50 mm, a width of between 10-25 mm.

9. The graft of claim 1, wherein the body is substantially free of fat and blood proteins.

10. The graft of claim 1, wherein the first layer is adhesively secured to the second layer.

11. The graft of claim 1, wherein the body comprises a unitary section of cancellous bone.

12. A flexible, compressible and compliant graft, the graft comprising a strip of bone forming a body having a length, a width and a thickness, wherein the thickness is between 4 mm and 6.5 mm and is less than half the length and half the width, the body further comprising:
    a first layer of porous demineralized bone extending the length and width of the body; and
    a second layer of porous mineralized bone extending along an outer surface of the strip that is continuously adjacent to the first layer, wherein the second layer has a thickness that is less than 1.5 mm that varies by less than 10% along the entire second layer;
    wherein the body had a density that is less than 2.6e-4 g/mm$^3$ and a mean bending thickness that is less than about 1.2 mNm.

* * * * *